(12) United States Patent
Asano et al.

(10) Patent No.: US 6,919,081 B1
(45) Date of Patent: Jul. 19, 2005

(54) LAK ACTIVITY POTENTIATOR ORGINATING IN SHITAKE MUSHROOM HYPHAE EXTRACT AND LAK ACTIVITY POTENTIATING PREPARATIONS CONTAINING THE SAME

(75) Inventors: Kenji Asano, Osaka (JP); Yukiko Matsuda, Osaka (JP); Yutaka Tajima, Saga (JP)

(73) Assignees: Kobayashi Pharmaceutical Co., Ltd., Osaka (JP); Hitoshi Nagaoka, Chiba (JP)

( * ) Notice: Subject to any disclaimer, the term of this patent is extended or adjusted under 35 U.S.C. 154(b) by 0 days.

(21) Appl. No.: 09/856,718

(22) PCT Filed: Nov. 26, 1999

(86) PCT No.: PCT/JP99/06616

§ 371 (c)(1),
(2), (4) Date: Jan. 28, 2002

(87) PCT Pub. No.: WO00/32212

PCT Pub. Date: Jun. 8, 2000

(Under 37 CFR 1.47)

(30) Foreign Application Priority Data

Nov. 27, 1998 (JP) ........................................... 10-353927
Nov. 27, 1998 (JP) ........................................... 10-353928

(51) Int. Cl.[7] .............................................. A61K 35/78
(52) U.S. Cl. .................. 424/195.15; 424/439; 424/442; 435/254.1
(58) Field of Search ........................... 424/195.15, 439, 424/442; 435/254.1

(56) References Cited

U.S. PATENT DOCUMENTS 4,461,760 A * 7/1984 Sugano et al.
2004/0038330 A1 2/2004 Nagaoka

FOREIGN PATENT DOCUMENTS

JP 7-173070 7/1995
JP 2000-159686 * 6/2000

OTHER PUBLICATIONS

Anticancer Research, vol. 13, No. 5c, p1773–1776, 1993 "Augmentation of Lymaphpkine–Activated Killer Cell Activity by Lentinan" Masaji Tani et al, p1776.

International Journal of Immunopharmacology, vol. 14, no4, p. 535–539, 1992 "Enhanced Induction of Lymphokine–Activated Killer Activity After Lentinan Administration in Patients with Gastric Carcinma" Shinya Arinaga et al, See p. 535, right column, lines 1–3.

* cited by examiner

*Primary Examiner*—Susan D. Coe
(74) *Attorney, Agent, or Firm*—Birch, Stewart, Kolasch & Birch, LLP.

(57) ABSTRACT

It is an object of the present invention to provide immunopotentiators and immunotherapeutic formulations available at low cost and having a benign side effect profile. According to the present invention, an LAK activity enhancer containing an extract of Lentinus edodes mycelium and an LAK activity-enhancing formulation containing said enhancer are provided.

8 Claims, 4 Drawing Sheets

LAK ACTIVITY POTENTIATOR ORGINATING IN SHITAKE MUSHROOM HYPHAE EXTRACT AND LAK ACTIVITY POTENTIATING PREPARATIONS CONTAINING THE SAME

This application is the national phase under 35 U.S.C. § 371 of PCT International Application No. PCT/JP99/06616 which has an International filing date of Nov. 26, 1999, which designated the United States of America and was not published in English.

FIELD OF THE INVENTION

The present invention relates to the immunological field. In particular, it relates to immune activity enhancers and therapeutic formulations containing an extract of Lentinus edodes mycelium. And more particularly, it relates to materials useful for enhancing LAK activity and LAK activity-enhancing formulations containing the extract.

PRIOR ART

The activity of the immune system can be classified into two modes of action: Cell-mediated immunity and humoral immunity. Humoral immunity refers to an immune response involving antibodies, while cell-mediated immunity refers to an immune response produced by cells acting directly on a target.

Lymphocytes play the main role in this cell-mediated immune response and often target cell surface substances as antigens. Cell-mediated immunity is thought to be also involved in immune response against tumor, intracellular parasites, and viruses, transplantation, some drug hypersensitivity and some autoimmune diseases. Generally, the reaction is often specific, but can also be non-specific.

For example, it is known in tumor immunology that tumor cells possess tumor antigens. That is, it is known that there are two types of antigens, one type consisting of tumor-specific antigens (TSA) and the other of tumor-associated antigens (TAA) which is also present in normal cells at a very low level, and upregulated with malignant transformation.

These tumor antigens are expressed by alteration in a genetic sequence or by mutation of autologous cells. A common therapy used against tumor cells having abnormal antigenic expression is immunotherapy, including immunization with a tumor antigen or administration of a drug which enhances the immune function. It is generally known that natural killer (NK) cells demonstrate higher tumor cell-destroying activity than normal cells and that immunotherapy can also enhance the activity of NK cells. NK cells are cytotoxic lymphocytes also present in normal individuals and are known to exhibit MHC antigen-nonrestricted cytotoxicity against tumor cells, virus-infected cells or the like. However, it has been recently shown that tumor cells exist which are resistant to even NK cells.

Dr. S. Rosenberg of the United States National Cancer Institute (NCI) found that incubation of peripheral lymphocytes with interleukin 2 (IL-2) can induce killer cells showing cytotoxicity to a wide range of target cancer cells, including autologous cancer cells, and that these killer cells can kill even NK cell-resistant cancer cells (see Japanese patent public disclosure No. 116518/87). These killer cells were named lymphokine activated killer (LAK) cells. LAK cells do not consist of a cytologically homogeneous population and are known to include NK cells and killer T-cells.

Recently, adoptive immunity has been attempted wherein peripheral lymphocytes from a patient are activated with IL2 in a cell culture system, and then LAK cells showing antitumor activity are reinfused into the patient (LAK therapy). It has been reported that remission from terminal cancer has been achieved or tumor growth-inhibited by the use of adoptive immunotherapy involving repeated administration of such LAK cells. However, IL-2-mediated LAK therapy involves a number of problems such as the physical stress associated with the isolation of a great number of leukocytes, the high cost of performing mass culture of isolated leukocytes, or the use of expensive IL-2, etc, and, moreover, IL-2 administration often causes serious side effects.

Specifically, it is known that LAK adoptive immunotherapy using IL-2 causes side effects such as general prostration, chills, fever, hypoalbuminemia, anemia, eosinophilia and that these side effects are more serious than those caused by administration of IL-2 alone. More notably, some important side effects are strongly associated with the cytotoxicity of LAK cells against normal cells. It is also reported that such cytotoxicity of LAK cells against hematopoietic stem cells induces anemia and thrombocytopenia, as well as causing in vitro damages to lymphocytes, macrophages and vascular endothelial cells. Moreover, IL-2 administered via the oral route is poorly absorbed and must therefore mainly be administered via injection and direct administration at the present time.

Thus, there is a demand for the development of therapeutic agents capable of overcoming these disadvantages, especially agents that could enhance the LAK activity of lymphocytes without using IL-2 or pharmaceutical agents containing such agents.

Anticancer agents are generally targeted at abnormal growth of cancer cells and can be classified by target into nucleic acid biosynthesis inhibitors such as alkylating agents, nucleic acid biosynthesis substrate analogs, antibiotics, steroid hormones, etc. and mitotic inhibitors such as plant alkaloids.

However, such anticancer agents also cause noticeable side effects with regard to normal proliferative cells such as bone marrow, gastrointestinal epithelium, and hair follicle. That is, they generally cause nausea, vomiting, ulcers of the mouth and small bowel, diarrhea, epilation, bone marrow inhibition leading to underproduction of major blood components, and so on, irrespective of the administration route.

Some bacteria foods and other naturally occurring substances are known to have anticancer properties. Bacteria and food-tye substance are generally far preferential for use as anti-cancer agents due to their generally benign nature and low side-effect profile. Many attempts have been made to cure cancer by using bacteria, as shown in reports relating to Coley's toxin consisting of a culture filtrate of Serratia marcesens and Streptococcus pyogenes (1964); treatment of leukemia with BCG (Mathe, G., Adv. Cancer Res., 14, 1, 1971); tumor regression in guinea pigs (Zbar, B., et al., J. Natl. Cancer Inst., 48, 831, 1971); and effectiveness of administration of yeast cell wall polysaccharide against transplanted tumor cells such as sarcoma 180, for example.

Especially, a great amount of research has been conducted into the anticancer effect of polysaccharides derived from yeast such as yeast glucan and yeast mannan, from other bacteirum, from lichens and from basidiomycetes. Among them, commercial products currently available on the market as anticancer immunopotentiators include Krestin derived from the cultured mycelia of kawaratake (Coriolus versicolor, Basidiomycetes: Polyporaceae) (booster of immune function of hosts, Kureha Chemical Industry and Sankyo Co.Ltd.), a polysaccharide derived from shiitake (Lentinus edodes) called lentinan and a polysaccharide derived from suehirotake (Schizophyllum Commune).

Lentinus edodes (Shiitake) is a common edible mushroom found in both Japan and China, and has been cultivated in Japan for around 300 years. It has been recently elucidated for its pharmacological effects and effective ingredients and reported to have various effects, such as growth inhibition effects on transplanted tumor cells in the large bowel and liver in rats and mice (Sugano N. et al., Cancer Letter, 27:1. 1985; Suzuki Y. et al., Journal of the Japan Society of Coloproctology, 43:178, 1990); mitogenic effect (Tabata T. et al., Immunopharmacology, 24:57, 1992; Hibino et al., Immunopharmacology, 28:77, 1994), etc.

DISCLOSURE OF THE INVENTION

The present inventors researched the immunopotentiating activity, antitumor activity and/or anticancer activity of Lentinus edodes with a view to providing an inexpensive immunotherapeutic agent having few side effects.

The present invention was accomplished on the basis of the finding that an extract of the mycelium, which is a precursor to the edible fruiting body of Lentinus edodes, has a far higher immunopotentiating activity, antitumor activity and/or anticancer activity than the fruiting body and that said extract also has an LAK activity-enhancing activity.

According to the first aspect of the present invention, therefore, an LAK activity enhancer containing an extract of Lentinus edodes mycelium is provided.

"LAK activity" refers to the cytotoxic activity of cytotoxic T-lymphocytes, which attacks tumors unrecognizable by lymphocytes having NK activity but which have little influence on autologous normal cells. "LAK activity-enhancing" refers to the effect of enhancing this LAK activity, that is directly or indirectly inducing the production of LAK cells from lymphocytes or further enhancing the activity of existing LAK cells.

Enhancement of LAK activity increases antitumor activity of LAK cells, which leads to an improvement in the function of the cell-mediated immune system. Thus, the present invention can be applied not only to treatments for improving antitumor activity but also to treatments for improving the immune function.

Lymphocytes derived from peripheral blood may be treated with LAK activity enhancers of the present invention to enhance LAK activity. They may directly act on lymphocytes derived from peripheral blood preferably at an extract of Lentinus edodes mycelium concentration of 1 µg or more per $10^6$ lymphocytes or 1 µg or more per 1 ml of peripheral blood. LAK activity enhancers of the present invention may be used in LAK therapy in place of IL-2.

LAK activity enhancers of the present invention may consist of an extract of Lentinus edodes mycelium on its own or may further contain materials other than an extract of Lentinus edodes mycelium. The range of such materials is not limited so long as the LAK activity enhancing-activity of the extract of Lentinus edodes mycelium is not affected by their use.

LAK activity enhancers of the present invention may also be combined with other materials having an immunopotentiating activity and antitumor activity and/or anticancer activity.

According to the second aspect of the present invention, an LAK activity-enhancing formulation comprising an LAK activity enhancer containing an extract of Lentinus edodes mycelium is provided.

LAK activity-enhancing formulations of the present invention may be the extract of Lentinus edodes mycelium itself or pharmaceutical or veterinary formulations comprising an LAK activity enhancer containing an extract of Lentinus edodes mycelium and a pharmaceutically acceptable carrier.

LAK activity-enhancing formulations of the present invention may be suitable for oral administration or injection or percutaneous administration.

LAK activity-enhancing formulations of the present invention may be in the form of a food, drink or feed.

LAK activity-enhancing formulations of the present invention may be used for treating tumor and/or cancer. LAK activity-enhancing formulations of the present invention do not specifically attack specific tumor cells, because they induce LAK cells. Therefore, LAK activity-enhancing formulations of the present invention can be used for treating various tumors, either epithelial or non-epithelial.

LAK activity-enhancing formulations of the present invention may also be used for treating other diseases than tumor or cancer, such as the improvement of the immune function. Specifically, LAK activity-enhancing formulations of the present invention may also be used for the improvement of immune function compromised by immunocompromising therapies or accidents such as radiation, autoimmune diseases, infectious diseases, etc.

LAK activity-enhancing formulations of the present invention can also be used as prophylactic agents against various diseases. For example, they may be administered to prevent tumor and/or cancer or to prevent bacterial or viral infections.

LAK activity-enhancing formulations of the present invention may be used in combination with other drugs such as antitumor and/or anticancer agents such as immunopotentiators, antibiotics, analgesics, antiinflammatory agents, etc.

According to the third aspect of the present invention, a method for treating tumor and/or cancer comprising administering an effective amount of said LAK activity-enhancing formulation is provided.

The method for treating tumor and/or cancer of the present invention may be used in combination with other therapies such as other chemotherapy, surgical treatment, radiation, thermotherapy, etc.

According to the fourth aspect of the present invention, a use of an LAK activity enhancer for obtaining a drug used for treating tumor and/or cancer is provided.

In order to obtain a drug used for treating tumor and/or cancer, LAK activity enhancers of the present invention may be used in combination with other materials having an immunopotentiating activity and antitumor activity and/or anticancer activity.

BRIEF DESCRIPTION OP THE DRAWINGS

THE MOST PREFERRED EMBODIMENTS OF THE INVENTION

Figure 1:
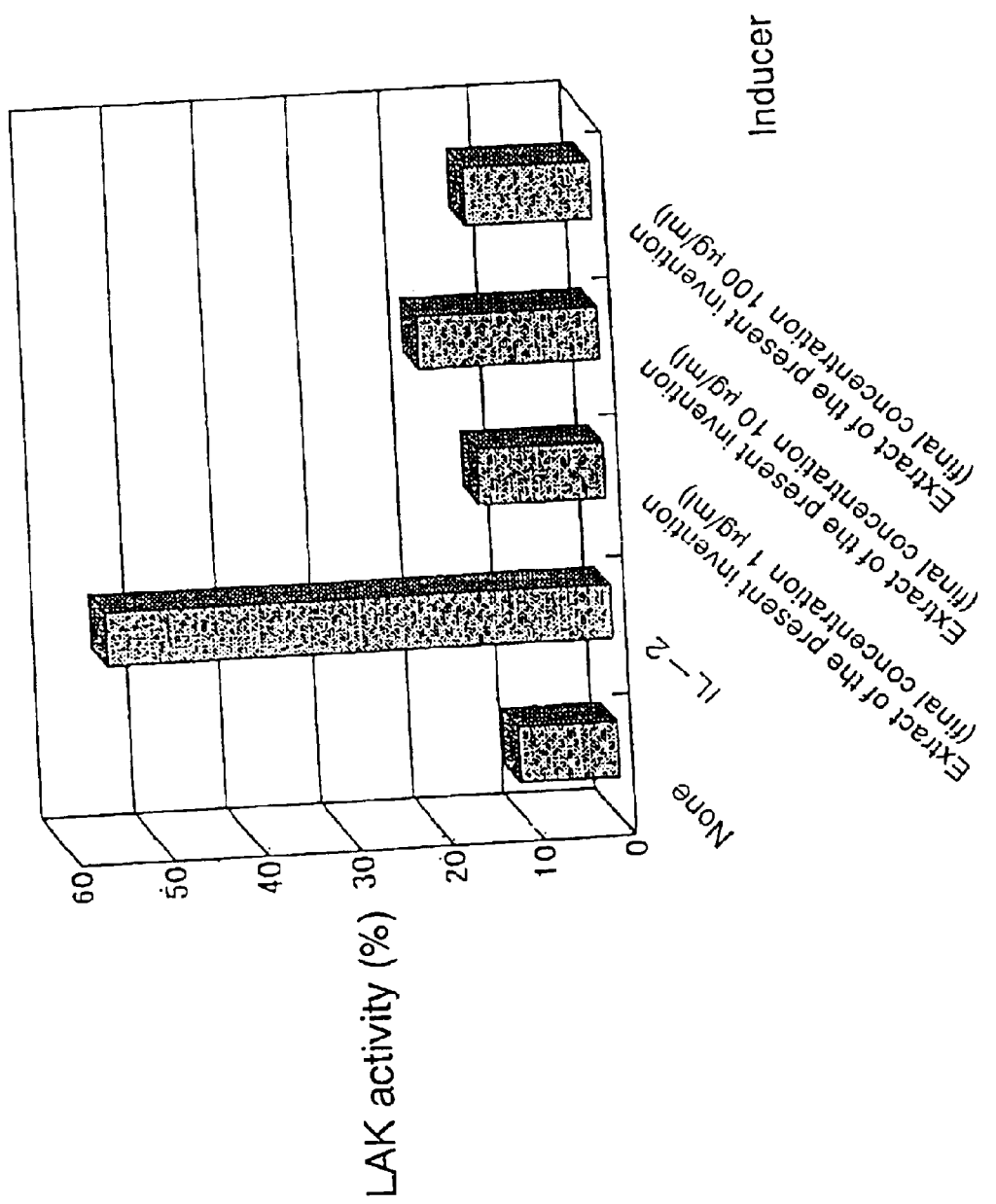
FIG. 1 is a bar graph showing the LAK activity-enhancing effect of the extract of Lentinus edodes mycelium directly added to peripheral blood as in comparison with IL-2.

An extract of Lentinus edodes mycelium contained in LAK activity enhancers of the present invention refers to an extract obtained by crushing and decomposing mycelia grown from Lentinus edodes cultured on a solid medium, or a solid medium itself containing Lentinus edodes mycelia in the presence of water and an enzyme.

An extract of Lentinus edodes mycelium used herein is preferably obtained by, but not specifically limited to, the following process.

Lentinus edodes spawn is inoculated on a solid medium based on bagasse (sugar cane residue) and defatted rice bran to grow mycelia, and then the solid medium containing the grown mycelia is delignified to enable about 30% by weight or less to pass through a 12-mesh sieve.

To this delignified solid medium are added water and one or more enzymes selected from cellulase, protease or glucosidase while maintaining said solid medium at a temperature of around 30–55° C., and said solid medium is crushed and ground in the presence of said enzyme so that at least 70% by weight of bagasse fiber is able to pass through a 12-mesh sieve. Then, the temperature is raised to 80–100° C. to ensure inactivation of the enzyme and sterilization, and the resulting suspension is filtered to give an extract of Lentinus edodes mycelium.

The extract of Lentinus edodes mycelium as prepared above may be directly used in LAK activity enhancers or LAK activity-enhancing formulations of the present invention, but conveniently concentrated and freeze-dried into powder to be stored and used in various forms. The freeze-dried product is a brown powder with hygroscopic characteristics and has a peculiar taste and odor.

LAK activity enhancers containing the prepared extract of Lentinus edodes mycelium (or the extract of Lentinus edodes mycelium on its own) may be used in LAK therapy in place of IL-2 to enhance the immune activity against tumor of the subject.

LAK therapy generally comprises the steps of culturing in vitro lymphocytes from the subject with IL-2 to induce LAK cells from the lymphocytes, and reinfusing the LAK cells into the subject. At the step of reinfusing LAK cells into the subject, IL-2 may be (directly) cocurrently administered.

LAK activity enhancers containing the extract of Lentinus edodes mycelium of the present invention may be cultured in vitro with lymphocytes from the subject (human, animals, etc.) to induce LAK cells or may be (directly) cocurrently administered to the subject at the step of reinfusing the cultured lymphocytes to the subject. They may be used in combination with other antitumor and/or anticancer agents.

LAK activity enhancers containing the extract of Lentinus edodes mycelium of the present invention may be directly added to peripheral blood collected from the subject, but preferably sterilized with acetone before being added.

LAK activity enhancers containing the extract of Lentinus edodes mycelium of the present invention can be directly added to peripheral blood collected from the subject preferably at a concentration expressed as the extract of Lentinus edodes mycelium of 1 $\mu$g–1 mg/$10^6$ lymphocytes, more preferably 10 $\mu$g–100 $\mu$g/$10^6$ lymphocytes, most preferably 10 $\mu$g–50 $\mu$g/$10^6$ lymphocytes. The dose per ml of peripheral blood, which partially depends on the level of lymphocytes in peripheral blood, approximately represents 1 $\mu$g–2.5 mg, preferably 10 $\mu$g–250 $\mu$g, more preferably 10 $\mu$g–125 $\mu$g.

LAK activity-enhancing formulations comprising an LAK activity enhancer containing the extract of Lentinus edodes mycelium of the present invention can be directly administered to the subject to enhance the anti-tumor immune activity of the subject, thereby providing an effect comparable to the effect elicited by LAK therapy using IL-2.

Induction of LAK cells in the subject such as a human or animals by directly administering the LAK activity enhancers of the present invention may make it possible to reduce physical stress associated with the isolation of a great number of leukocytes and the high cost resulting from producing mass culture. In addition, the use of LAK activity-enhancers of the present invention can also reduce the risk of contamination during the isolation of blood from the subject and reinfusion can also be reduced.

LAK activity-enhancing formulations of the present invention are administered most preferably, but are not limited to, the oral route in view of the least stress imposed on the subject and the like. They may also be administered via intravenous, intracutaneous, subcutaneous or intramuscular injection, or percutaneous, nasal, enteral or other routes.

Suitable dosage forms of LAK activity-enhancing formulations of the present invention include, but are not limited to, tablets, capsules, powders, granules, solutions, syrups, injections, creams, ointments, patches, sprays, suppositories, etc.

Pharmaceutically acceptable carriers that can be optionally mixed with LAK activity-enhancing formulations of the present invention include, but not limited to, excipients such as lactose, dextrose, starch, crystalline cellulose; binders such as starch, gelatin, methyl cellulose, polyvinylpyrrolidone; disintegrators such as starch, calcium carboxymethylcellulose, carboxymethyl starch; lubricants such as talc, stearates; coating agents such as sucrose, talc, gelatin; as well as various brighteners, flavoring agents, colorants, corrigents, solubilizers, stabilizers, suspending agents, absorbefacients or the like known in the art depending on the purpose. For use as injections, various diluents commonly used in this field of art such as water or ethyl alcohol can be used.

The route of administration, dose, frequency or others of LAK activity-enhancing formulations of the present Invention are determined taking into account the age, weight, condition and other factors of the subject.

The extract of Lentinus edodes mycelium contained in LAK activity-enhancing formulations of the present invention is highly safe as has been traditionally ingested as a component of food. Therefore, the dose is not be strictly limited. For example, the extract of Lentinus edodes mycelium is normally administered preferably at a dose of 100 mg–10000 mg 2–3 times daily, more preferably 500 mg–5000 mg three times daily, most preferably 1000 mg–1500 mg three times daily. It may be administered in combination with other drugs such as antitumor and/or anticancer agents such as immunopotentiators, antibiotics, analgesics, antiinflammatory agents, etc.

LAK activity-enhancing formulations of the present invention can also be provided in the form of a food. Preferred forms of food include powders, granules, pastes, jellies, etc. Granules desirably are supplemented with sugars such as lactose to add a sweet taste. LAK activity-enhancing formulations of the present invention can also be provided in the form of a drink. These foods or drinks may be supplemented with vitamins, minerals such as calcium, alcohols, deodorants such as polyphenols in addition to the extract of Lentinus edodes mycelium. These foods or drinks may include the categories of specific health foods, medical foods or the like.

LAK activity-enhancing formulations of the present invention can also be provided in the form of a feed or feed additive. LAK activity-enhancing formulations of the present invention can be used as a feed or feed additive for domestic animals to treat and/or prevent tumor occurring in the domestic animals or to treat and/or prevent bacterial or viral infections in domestic animals.

As a result, the amount of therapeutic agents such as antibiotics currently used can be reduced, thereby reducing farming costs. Another advantage is that the period during which shipment of animals is suspended due to the administration of antibiotics can be shortened.

LAK activity enhancement with LAK activity enhancers of the present invention can be confirmed by, but not limited to, the procedure below according to the method of Takagi et al. (Clinical Immunology, 19:245–249, 1987).

LAK activity test

LAK activity can be determined by $^{51}$Cr release assay, [$^{3}$H] uridine assay or the like. In terms of convenience and objectivity, the $^{51}$Cr release assay is preferably used.

The $^{51}$Cr release assay is one of methods for in vitro determining the cytotoxicity against target cells of LAK cells induced from lymphocytes treated with an LAK activity enhancer, and comprises the steps of;

(i) adding $^{51}$Cr-labeled sodium chromate to the target cells to label the target cells, (ii) reacting the labeled target cells with induced LAK cells, and (iii) measuring the amount of $^{51}$Cr released into the cell culture supernatant from the target cells bursted by the LAK cells.

Subcultured cells used as target cells in the $^{51}$Cr release assay are preferably Daudi cells or Raji cells. Target cells cultured in a culture flask or the like are collected by centrifugation, and labeled with $^{51}$Cr via incubation in a 5% $CO_2$ incubator at 37° C. for 1–2 hours after 100–150 $\mu$Ci $^{51}$Cr labeled-sodium chromate has been added. Culture media for target cells are those suitable for the growth of the cells used, and include, for example, liquid media such as RPMI 1640 or F-12 appropriately supplemented with serum, antibiotics, etc.

Cultured target cells are washed with PBS three times, and then suspended in a culture medium at a density of 1 ×10$^6$ cells/ml to serve for assay.

To induce LAK cells lymphocytes are isolated from peripheral blood of the subject. Heparin is added to peripheral blood from the subject, and monocytes at the interface are separated by density gradient centrifugation on Ficoll-Conray solution (s.g.=1.077). The separated monocytes are washed with PBS (pH 7.4, without Ca and Mg) 2–3 times and then suspended in a culture medium (preferably, RPMI 1640 medium (Gibco) containing FBS (inactivated fetal bovine serum) and/or antibiotics, if desired) at a density of 1×10$^6$ cells /ml. This suspension is transferred to a Petri dish which has been precoated with autoserum (plasma) at 37° C. for 15 minutes, and incubated at 37° C. for 1 hour. Unattached cells are recovered as lymphocyte fractions.

The lymphocytes as prepared above are suspended in a culture medium at a predetermined concentration, preferably 1×10$^5$–10$^6$ cells/ml.

The extract of Lentinus edodes mycelium is added to the medium as used for preparing the lymphocyte-suspending solution at a final concentration of about 1–100 $\mu$g/ml.

Predetermined amounts of the lymphocyte-suspending solution and extract-containing medium are added to wells of a culture plate. In parallel, predetermined amounts of the lymphocyte-floating solution and the medium not containing the extract of Lentinus edodes mycelium are added to wells as an extract-free control. Then, the culture plate is statically incubated in a $CO_2$ incubator at room temperature for 3 days.

When a 96-well U-bottom microtest plate is used, for example, 100 $\mu$l of the lymphocyte-floating solution is preferably added to each well at a density of 1×10$^4$ to 1×10$^5$ cells/well. The number of cells per well can be appropriately determined by those skilled in the art in accordance with the well volume, the activity of LAK cells, the sensitivity of target cells to LAK cells, etc.

Thus, lymphocytes derived from the subject are cultured in the presence of the extract of Lentinus edodes mycelium of the present invention at various concentrations (including zero) to induce effector cells. As used herein, the term effector cells refers to cells subjected to said culture treatment for 3 days and includes both lymphocytes cocultured with an LAK activity enhancer (lymphocytes treated with an LAK activity enhancer) and lymphocytes cultured in the medium alone without LAK activity enhancer (lymphocytes treated under the extract-free condition).

Cultured lymphocytes (effector cells) are recovered from the well and resuspended in fresh RPMI 1640 medium containing 10% FBS (1×10$^6$ cells/ml).

In the assay for determining cytotoxicity, each well containing said target cells is further supplied with a predetermined amount of the floating solution containing said various effector cells (lymphocytes treated with LAK active enhancer or those under the extract-free condition) at a density of 1×10$^5$–1×10$^6$ cells/ml for experimental dissociation, 1N HCl in an amount equal to the effector-floating solution for maximum dissociation, or the medium alone in an amount equal to the effector-floating solution for natural dissociation. Then, cells are collected at the bottom of the well of the culture plate using a plate centrifuge or the like, and then incubated in a 5% $CO_2$ incubator at 37° C. for a predetermined period (for example, 2–5 hours).

After completion of the incubation, the radioactivity of $^{51}$Cr released in the culture supernatant in the culture supernatant in each well is measured using a scintillation counter or the like.

The term "maximum dissociation" refers to the total amount of $^{51}$Cr released when all the target cells are destroyed. Maximum dissociation can be determined by, for example, lysing target cells via incubation in a culture medium containing 1N HCl under predetermined conditions in the absence of effector cells and measuring the amount of $^{51}$Cr released in the culture supernatant.

The term "experimental dissociation" refers to the amount of $^{51}$Cr released by cytotoxicity of effector cells against target cells and natural death of target cells when effector cells are added to target cells. Experimental dissociation can be determined by, for example, incubating target cells under the same conditions as those for maximum dissociation with the exception of adding effector cells in place of 1N HCl to the culture medium and measuring the amount of $^{51}$Cr released in the culture supernatant.

The term "natural dissociation" refers to the amount of $^{51}$Cr released by natural death of target cells. Natural dissociation can be determined by, for example, incubating target cells under the same conditions as for maximum dissociation with exception of containing neither 1 N HCl nor effector cells and measuring the amount of $^{51}$Cr released in the culture supernatant.

The activation level of LAK cells is evaluated on the basis of the LAK activity calculated by equation (1) below.

$$LAK\ activity\ \% = \frac{\text{Experimental dissociation (cpm)} - \text{Natural dissociation (cpm)}}{\text{Maximum dissociation (cpm)} - \text{Natural dissociation (cpm)}} \times 100 \quad \text{Equation (1)}$$

The disclosure of JPA Nos. 353927/98 and 353928/98 on which the present application is based to claim the priority are incorporated herein as a whole as reference.

The following examples further illustrate the present invention but should not be taken as limiting the scope of the invention thereto. It will be appreciated by those skilled in the art that various changes and modifications can be made without departing from the spirit of the present invention.

EXAMPLES

Example 1

Preparation of an Extract of Lentinus Edodes Mycelium

A solid medium consisting of 90 parts by weight of bagasse and 10 parts by weight of rice bran was soaked with an appropriate amount of pure water, and then inoculated with Lentinus edodes spawn and allowed to stand in an incubator at controlled temperature and humidity to grow mycelia. After mycelia spread over the solid medium, the bagasse base was delignified to enable 24% by weight or less eto pass through a 12-mesh sieve. To 1.0 kg. of this delignified medium were added 3.5 L of pure water and 2.0 g of purified cellulase while maintaining the solid medium at 40° C. to prepare a medium-containing mixture.

Then, the medium-containing mixture was circulated by a variable speed gear pump, during which the solid medium was crushed and ground at the gears for about 200 minutes so that about 80% by weight of bagasse fiber is able to pass through a 12-mesh sieve. The medium-containing mixture was crushed and ground while the temperature of said mixture was gradually increased. Then, the medium-containing mixture was further heated to 90° C. to ensure inactivation of the enzyme and sterilization and allowed to stand at 90° C. for 30 minutes. The resulting medium-containing mixture was filtered through a 60-mesh filter cloth to give an extract of Lentinus edodes mycelium solution, which was-concentrated and then converted into a freeze-dried powder.

The extract of Lentinus edodes mycelium as prepared above contained 25.3% (w/w) carbohydrates determined by the phenol-sulfuric acid method, 19.7% (w/w) proteins determined by the Lowry method and 2.6% (w/w) polyphenols determined by the Folin-Denis method using gallic acid as standard. The extract of Lentinus edodes mycelium further contains 8% crude fat, 22% crude ash and about 20% soluble nitrogen-free materials other than carbohydrates.

The extract of Lentinus edodes mycelium had a sugar composition (%) as follows: Xyl 15.2, Ara 8.2, Man 8.4, Gul 39.4, Gal 5.4, GlcN 12.0, GluUA 11.3.

Example 2

Comparison of LAK Activities of the Extract of Lentinus Edodes Mycelium and IL-2

The extract of Lentinus edodes mycelium obtained in Example 1 was directly administred to peripheral blood collected from the subject to compare the LAK activity-enhancing effect with that of IL-2.

Heparin was added to peripheral blood from subject A and monocytes at the interface were separated by density gradient centrifugation on Ficoll-Conray solution (s.g.=1.077). The separated monocytes were washed with PBS (pH 7.4, without Ca and Mg) twice and then suspended in RPMI 1640 medium (Gibco) containing 10% FBS (inactivated fetal bovine serum) at a density of $1 \times 10^6$ cells /ml. This cell suspension was transferred to a Petri dish which had been precoated with autoserum (plasma) at 37° C. for 5 minutes followed by incubation at 37° C. for 1 hour, and then unattached cells were recovered as lymphocyte fractions.

The lymphocytes as prepared above were suspended in RPMI 1640 medium (Gibco) containing 10% FBS (inactivated serum) at $1 \times 10^6$ cells /ml. LAK activity enhancer-containing solutions were prepared by adding IL-2 at a final concentration of 25 U/ml or the extract of Lentinus edodes mycelium obtained in Example 1 at final concentrations of 1, 10, 100 or 1000 μg/ml to RPMI 1640 medium (Gibco) containing 10% FBS (inactivated serum).

To each well of a 96-well U-bottom microtest plate were added 100 μl of the lymphocyte-suspending solution and 100 μl of IL-2 or the LAK activity enhancer-containing solution containing the extract of Lentinus edodes mycelium at various concentrations (a total of 200 μl). As an extract-free-control, 100 μl of the lymphocyte-suspending solution and 100 μl of the extract-free medium (RPMI 1640 medium (Gibco) containing 10% FBS (inactivated serum)) were added. Then, the culture plate was statically incubated in a $CO_2$ incubator at room temperature for 3 days.

Cultured lymphocytes (effector cells) were recovered from the well and resuspended in fresh RPMI 1640 medium containing 10% FBS at a concentration of $1 \times 10^6$ cells/ml.

Target cells (Daudi cells from Dainippon Pharmaceutical) subcultured in RPMI 1640 medium containing 10% FBS were recovered by centrifugation, and incubated with 100–150 μCi/$10^6$ cells of $^{51}$Cr labeled-sodium chromate (New England Nuclear) in a 5% $CO_2$ incubator at 37° C. for 1 hour. Cultured cells labeled with $^{51}$Cr were washed with PBS three times, and then suspended in RPMI 1640 medium containing 10% FBS at a concentration of $1 \times 10^6$ cells/ml.

A 50 μl aliquot ($5 \times 10^4$ cells/well) of labeled target cells was added to each of wells of the microtest plate for maximum dissociation, natural dissociation and experimental dissociation. In addition, 100 μl of 1N HCl was added to each well for maximum dissociation, 100 μl of RPMI 1640 medium containing 10% FBS was added to each well for natural dissociation, and 100 μl of effector cells treated with 10 μg/ml of the extract of Lentinus edodes mycelium of the present invention at concentrations of 1, 10, 100 and 1000 μg/ml or 25 U/ml of IL-2 or the medium alone were added to each well for experimental dissociation. Here, each well for experimental dissociation, maximum dissociation and natural dissociation was not located around the outer periphery of the plate.

Then, the microtest plate was centrifuged at 800 rpm for 5 minutes on a plate centrifuge to collect cells at the bottom of the well, and then incubated in a 5% $CO_2$ incubator at 37° C. for 3.5 hours.

The culture supernatant in each well was collected by SOKEN-PET Σ-96 from the incubated plate, and the radioactivity was measured in a γ-scintillation counter.

LAK activity was calculated by equation (1) above.

The results are shown in Table 1 and FIG. 1.

TABLE 1

| Test No. | Inducer | LAK activity |
|---|---|---|
| 1 | None | 11% |
| 2 | IL-2 (final concentration: 25 U/ml) | 55% |
| 3 | Extract of Lentinus edodes mycelium (final concentration: 1 µg/ml) | 14% |
| 4 | Extract of Lentinus edodes mycelium (final concentration: 10 µg/ml) | 20% |
| 5 | Extract of Lentinus edodes mycelium (final concentration: 100 µg/ml) | 14% |

In order to examine the toxicity of the extract of Lentinus edodes mycelium to lymphocytes, lymphocytes was treated with the extract of Lentinus edodes mycelium as prepared in Example 1 at a final concentration of 1 mg/ml by the same procedure as described above and observed under a microscope to show that almost 100% of lymphocytes survived (data not shown).

Example 3

Optimal Concentration of the Extract of Lentinus Edodes Mycelium for LAK Activity The optimal concentration of the extract of Lentinus edodes mycelium to be directly added to peripheral blood collected from the subject was examined. LAK activity was calculated in the same manner as described in Example 2 with exception that the extract of Lentinus edodes mycelium as prepared in Example 1 was added at final concentrations of 1, 5, 10 and 100 µg/ml to peripheral blood collected from subjects B and C.

Figure 2:
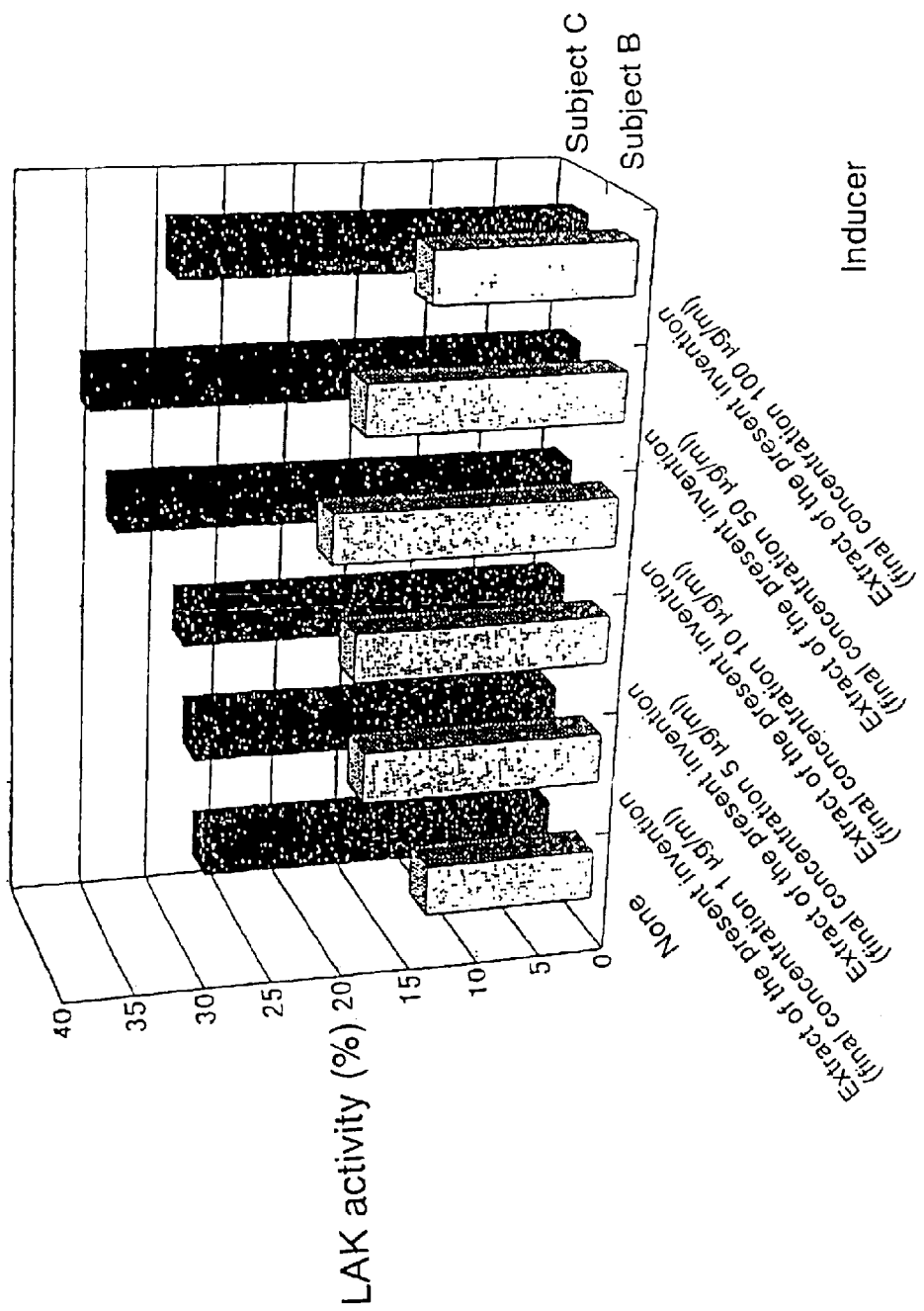
FIG. 2 is a bar graph showing the change of LAK activity with the concentration of the extract of Lentinus edodes mycelium directly added to peripheral blood.

The results are shown in Table 2 and FIG. 2.

As shown in Table 2 and FIG. 2, the extract of Lentinus edodes mycelium of the present invention shows the 5 highest LAK activity when it is added at a final concentration of 10 µg/ml or 50 µg/ml (i.e. 10 µg or 50 µg per $10^6$ lymphocytes). The dose to peripheral blood also depends on the proportion of lymphocytes in peripheral blood of the subject, but approximately corresponds to about 10–25 µg or 50–125 µg of the extract of Lentinus edodes mycelium per 1 ml of peripheral blood.

TABLE 2

| | | LAK activity Subject | |
|---|---|---|---|
| Test No. | Inducer | B | C |
| 1 | None | 13% | 27% |
| 2 | Extract of Lentinus edodes mycelium (final concentration: 1 µg/ml) | 18% | 28% |
| 3 | Extract of Lentinus edodes mycelium (final concentration: 5 µg/ml) | 19% | 29% |
| 4 | Extract of Lentinus edodes mycelium (final concentration: 10 µg/ml) | 21% | 34% |
| 5 | Extract of Lentinus edodes mycelium (final concentration: 50 µg/ml) | 19% | 36% |
| 6 | Extract of Lentinus edodes mycelium (final concentration: 100 µg/ml) | 15% | 30% |

Comparative Example 1

LAK Activity of Krestin

LAK activity-enhancing effect of an immunopotentiator Krestin was examined to compare it with the effect of the extract of Lentinus edodes mycelium of the present invention. LAK activity-enhancing effect of Krestin was evaluated in the same manner as described in Example 2 with exception that Krestin (from Kureha Chemical Industry) was added to peripheral blood collected from subject D at a final concentration of 1 mg/ml.

The final concentration of 1 mg/ml is the concentration said to be the most effective when Krestin is used to induce LAK cells.

Figure 3:
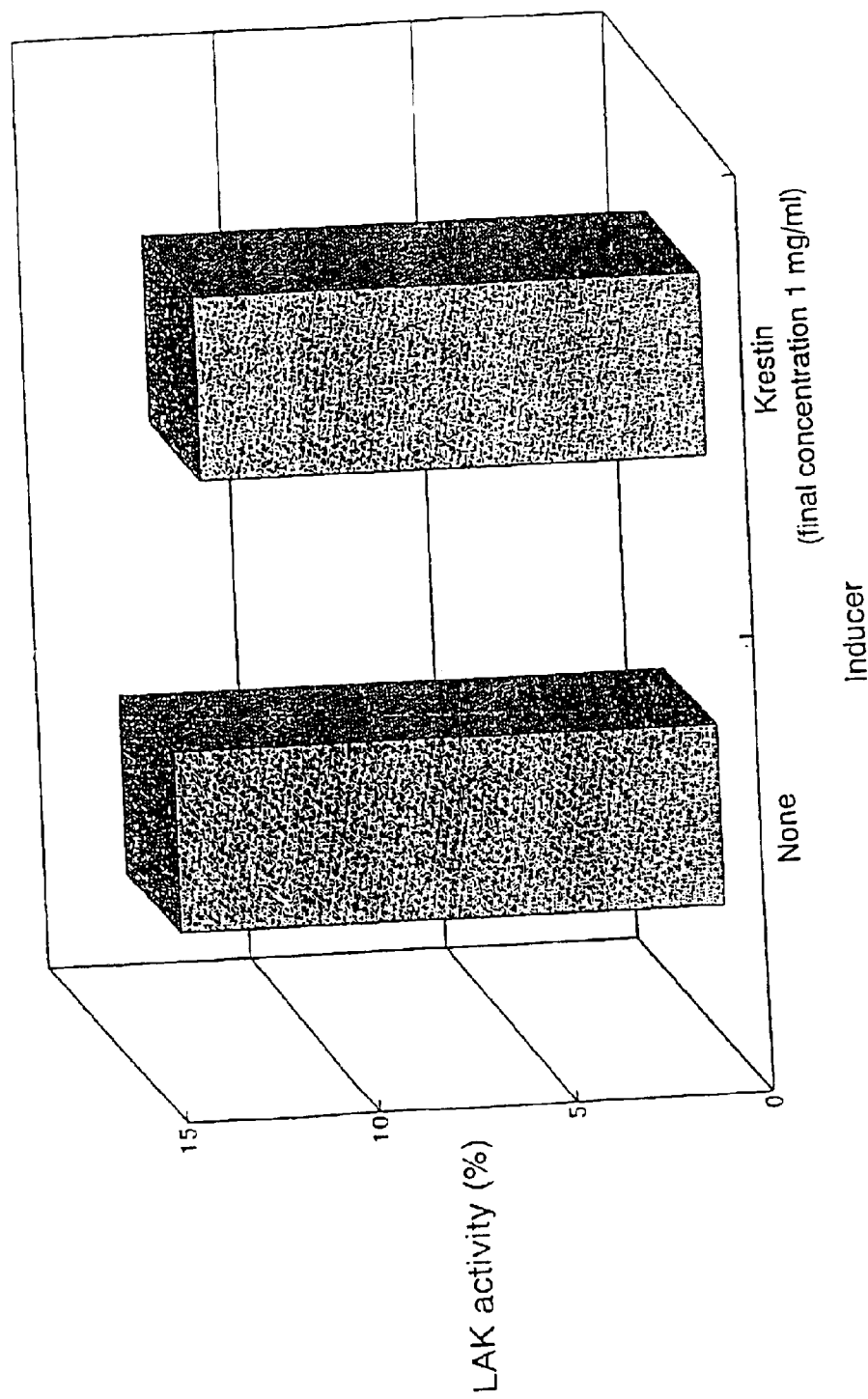
FIG. 3 is a bar graph showing the LAK activity obtained by directly adding Krestin to peripheral blood.

The results are shown in Table 3 and FIG. 3.

As shown in Table 3 and FIG. 3, the LAK-enhancing activity of Krestin was lower than that of a control not containing LAK activity enhancer even at the optimal concentration of 1 mg/ml.

TABLE 3

| Test No. | Inducer | LAK activity |
|---|---|---|
| 1 | None | 14% |
| 2 | Krestin (final concentration: 1 mg/ml) | 13% |

Example 4

Determination of LAK Activity Before and After Administration of a Formulation Containing the Extract of Lentinus Edodes Mycelium An LAK activity-enhancing formulation containing the extract of Lentinus edodes mycelium prepared in the same manner as described in Example 1 was administered to subjects B, C, E and F to evaluate the LAK activity-enhancing effect.

This LAK activity-enhancing formulation comprises 0.6 g of the extract of Lentinus edodes mycelium and 2.4 9 of lactose per 3 g of the formulation, and was administered at a dose of 6 g (1.2 g as the extract of Lentinus edodes mycelium) three times daily or a total of 3.6 g/day expressed as the extract of Lentinus edodes mycelium for a week. Peripheral blood was collected from each subject before administration and about 2 hours after the final administration, and LAK activity was determined in the same manner as described in Example 2.

Figure 4:
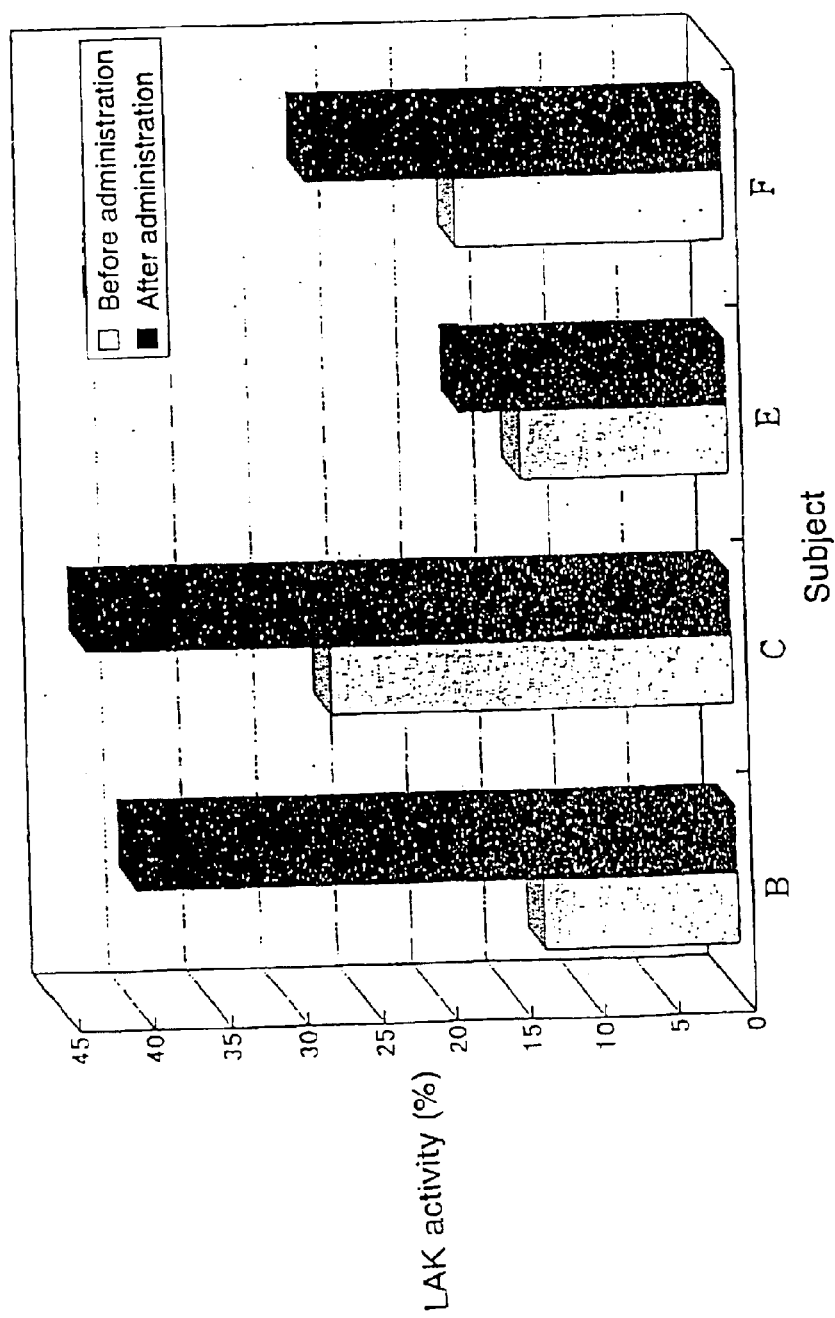
FIG. 4 is a bar graph showing the LAK activity in peripheral blood before and after oral administration of the extract of Lentinus edodes mycelium.

The results are shown in Table 4 and FIG. 4.

As shown in Table 4 and FIG. 4, the extract of Lentinus edodes mycelium of the present invention remarkably increased LAK activity in all of subjects B. C, E and F.

TABLE 4

| | LAK activity | | | |
|---|---|---|---|---|
| Subject | B | C | E | F |
| Before administration of LEM | 13% | 27% | 14% | 18% |
| After administration of LEM | 40% | 43% | 18% | 28% |

In order to examine side effects caused by the administration of the extract of Lentinus edodes mycelium, biochemical blood tests were performed on subjects B, C and E. The results are shown in Table 5. Throughout the period for administration of the extract of Lentinus edodes mycelium, subjects B. C, E and F did not show any side effects, such as generalized fatigue, chills, fever or digestive system symptoms.

As also shown in Table 5, any side effects were not observed by administration of the extract of Lentinus edodes mycelium of the present invention.

TABLE 5

| | Subject B | | Subject C | | Subject E | |
|---|---|---|---|---|---|---|
| | \multicolumn{6}{c}{Administration for 1 week} | | | | | |
| | Before | After | Before | After | Before | After |
| WBC (×10$^7$/µl) | 5.45 | 5.94 | 5.85 | 5.08 | 8.01 | 7.47 |
| RBC (×10$^6$/µl) | 4.56 | 4.61 | 4.99 | 4.85 | 4.89 | 4.65 |
| Hb (g/dl) | 14.2 | 14.2 | 14.4 | 13.8 | 15.5 | 14.8 |
| Ht (%) | 42.2 | 42.8 | 43.6 | 42.1 | 44.8 | 42.9 |
| MCV (fl) | 92.5 | 92.8 | 87.4 | 86.8 | 91.6 | 92.3 |
| MCH (pg) | 31.1 | 30.8 | 28.9 | 28.5 | 31.7 | 31.8 |
| MCHC (g/dl) | 33.6 | 33.2 | 33.0 | 32.8 | 34.6 | 34.5 |
| PLT (×10$^4$/µl) | 19.1 | 18.5 | 23.9 | 19.3 | 29.2 | 29.7 |
| RDW-SD (fl) | 43.7 | 44.6 | 43.5 | 43.6 | 43.7 | 44.8 |
| RDW-CV (%) | 12.8 | 13.0 | 13.4 | 13.6 | 13.0 | 13.3 |
| PDW (fl) | 14.0 | 13.4 | 11.6 | 12.6 | 13.3 | 13.2 |
| MPV (fl) | 11.1 | 10.9 | 10.0 | 10.2 | 10.6 | 10.4 |
| P-LCR (%) | 34.1 | 32.5 | 24.9 | 27.6 | 30.1 | 28.8 |
| Stab | 0.5 | 0.5 | 1.0 | 0.0 | 0.5 | 0.0 |
| Seg | 54.0 | 48.5 | 56.0 | 43.5 | 46.5 | 38.5 |
| Lym | 37.5 | 40.5 | 38.0 | 43.5 | 28.5 | 35.0 |
| Mono | 4.5 | 7.5 | 3.0 | 9.5 | 11.5 | 8.5 |
| Eo | 2.5 | 3.0 | 1.5 | 1.0 | 12.0 | 15.5 |
| Baso | 1.0 | 0.0 | 0.5 | 0.5 | 0.5 | 0.5 |
| TP (g/dl) | 6.6 | 6.9 | 7.7 | 7.5 | 8.0 | 7.7 |
| ALB (g/dl) | 3.9 | 4.1 | 4.4 | 4.3 | 4.8 | 4.7 |
| A/G | 1.44 | 1.46 | 1.33 | 1.34 | 1.50 | 1.57 |
| TTT (SHU) | 3.9 | 5.0 | 8.0 | 8.1 | 5.3 | 3.0 |
| ZTT (Kunk) | 8.6 | 8.4 | 12.6 | 12.4 | 6.3 | 4.9 |
| U-N (mg/dl) | 10.4 | 10.3 | 10.2 | 11.2 | 11.8 | 11.6 |
| U-A (mg/dl) | 5.6 | 5.9 | 5.4 | 5.2 | 6.1 | 5.9 |
| Creatinine (mg/dl) | 0.67 | 0.71 | 0.84 | 0.82 | 0.67 | 0.72 |
| Overall BIL (mg/dl) | 0.6 | 0.7 | 0.5 | 0.6 | 0.5 | 0.5 |
| Direct BIL (mg/dl) | 0.1 | 0.1 | 0.0 | 0.0 | 0.1 | 0.1 |
| Indirect BIL (mg/dl) | 0.5 | 0.6 | 0.5 | 0.6 | 0.4 | 0.4 |
| GLU (mg/dl) | 124 | 104 | 94 | 111 | 115 | 114 |
| AST (GOT) (IU/l) | 15 | 13 | 18 | 16 | 33 | 33 |
| ALT (GPT) (IU/l) | 29 | 30 | 20 | 20 | 45 | 57 |
| LD (LDH) (IU/l) | 142 | 139 | 171 | 152 | 380 | 343 |
| CK (CPK) (IU/l) | 121 | 131 | 227 | 177 | 317 | 224 |
| ALP (IU/l) | 131 | 136 | 156 | 148 | 174 | 162 |
| γ-GT (IU/l) | 12 | 14 | 23 | 23 | 225 | 240 |
| LAP (IU/l) | 45 | 40 | 80 | 73 | 134 | 120 |
| CHE (IU/l) | 2358 | 2593 | 2779 | 2749 | 3191 | 3299 |
| AMY (IU/l) | 78 | 87 | 107 | 93 | 59 | 54 |
| T-CHO (mg/dl) | 208 | 232 | 206 | 200 | 255 | 243 |
| HDLCHO (mg/dl) | 50 | 50 | 44 | 40 | 47 | 47 |
| T-G (mg/dl) | 135 | 210 | 270 | 303 | 451 | 359 |
| Na (mEq/l) | 141 | 142 | 140 | 141 | 139 | 141 |
| K (mEq/l) | 3.7 | 3.9 | 4.1 | 3.8 | 4.0 | 4.2 |
| Cl (mEq/l) | 106 | 107 | 105 | 107 | 103 | 104 |
| Ca (mEq/l) | 4.4 | 4.4 | 4.6 | 4.4 | 4.9 | 4.7 |
| I-P (mg/dl) | 3.3 | 3.1 | 3.0 | 2.7 | 3.5 | 3.2 |
| H | 0 | 0 | 0 | 0 | 1 | 0 |
| L | 0 | 0 | 0 | 1 | 1 | 0 |
| I | 0 | 1 | 1 | 1 | 1 | 1 |
| RA test | (−) | (−) | (−) | (−) | (−) | (−) |
| CRP (mg/dl) | 0.03 | 0.06 | 0.02 | 0.01 | 0.07 | 0.12 |
| ANA | <40 | <40 | <40 | <40 | <40 | <40 |
| ANA pattern | (−) | (−) | (−) | (−) | (−) | (−) |
| CH50 (CH50/ml) | 33.0 | 33.0 | 45.0 | 42.0 | 53.0 | 52.0 |

INDUSTRIAL APPLICABILITY

LAK enhancers containing the extract of Lentinus edodes mycelium of the present invention showed similar effects to those of IL-2 with no direct toxicity to lymphocytes when they were directly administered to peripheral blood. They are available at far lower cost as compared with IL-2. Therefore, they can be substituted for expensive IL-2 which also has the disadvantage of causing strong side effects.

Formulations containing the extract of Lentinus edodes mycelium of the present invention could remarkably increase LAK activity with no side effects even by direct administration. Therefore, formulations containing the extract of Lentinus edodes mycelium of the present invention are useful as an immunopotentiator capable of increasing LAK activity with a benign side-effect profile by direct administration such as oral administration without using LAK therapy.

What is claimed is:

1. A method for enhancing LAK activity which comprises administering to a mammal a therapeutically effective amount of LAK activity enhancer containing an extract of Lentinus edodes mycelium, which is prepared by:
   preparing a suspension by crushing and delignifying a solid medium containing Lentinus edodes mycelia in the presence of water and one or more of additive enzymes(s) selected from the group consisting of cellulase, protease and glucosidase, wherein said solid medium is based on bagasse and defatted rice bran; and
   raising the temperature of said suspension to 80–100° C. to inactivate the enzyme(s).

2. The method of claim 1 wherein said LAK activity enhancer acts on lymphocytes derived from peripheral blood.

3. The method of claim 1 wherein said LAK activity enhancer contains an extract of Lentinus edodes mycelium at a concentration of 1 µg or more per 10$^6$ lymphocytes.

4. The method of claim 1 wherein said LAK activity enhancer further comprises a pharmaceutically acceptable carrier.

5. The method of claim 1 wherein said LAK-activity enhancer is orally administered.

6. The method of claim 1 wherein said LAK activity enhancer is in the form of a food, drink or feed.

7. The method of claim 1 wherein said LAK activity enhancer is administered by injection or a percutaneous route.

8. A method for treating tumor and/or cancer by enhancing LAK activity, which comprises administering a therapeutically effective amount of a LAK activity enhancer containing an extract of Lentinus edodes mycelium that has been extracted from a solid medium comprising bagasse and defatted rice bran which contains Lentinus edodes mycelia and which is obtainable by the following steps:
   delignifying the solid medium;
   adding water and one or more enzymes selected from the group consisting of cellulase, protease and glucosidase to the delignified solid medium;
   crushing and grinding said delignified solid medium in the presence of said enzyme(s); and
   inactivating enzyme(s).

* * * * *

UNITED STATES PATENT AND TRADEMARK OFFICE
CERTIFICATE OF CORRECTION

| | | |
|---|---|---|
| PATENT NO. | : 6,919,081 B1 | Page 1 of 1 |
| APPLICATION NO. | : 09/856718 | |
| DATED | : July 19, 2005 | |
| INVENTOR(S) | : Kenji Asano et al. | |

It is certified that error appears in the above-identified patent and that said Letters Patent is hereby corrected as shown below:

On the cover page, item [54], change (the Title) as follows:

"LAK ACTIVITY POTENTIATOR ORIGINATING IN SHITAKE MUSHROOM HYPHAE EXTRACT AND LAK ACTIVITY POTENTIATING PREPARATIONS CONTAINING THE SAME"

To:

--LAK ACTIVITY ENHANCERS DERIVED FROM EXTRACT OF LENTINUS EDODES MYCELIUM AND LAK ACTIVITY-ENHANCING FORMULATIONS CONTAINING THE EXTRACT--

Signed and Sealed this

Sixth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 6,919,081 B1  Page 1 of 1
APPLICATION NO. : 09/856718
DATED : July 19, 2005
INVENTOR(S) : Kenji Asano et al.

It is certified that error appears in the above-identified patent and that said Letters Patent is hereby corrected as shown below:

On the cover page, item [54] and Column 1, lines 1-5, change (the Title) as follows:

"LAK ACTIVITY POTENTIATOR ORIGINATING IN SHITAKE MUSHROOM HYPHAE EXTRACT AND LAK ACTIVITY POTENTIATING PREPARATIONS CONTAINING THE SAME"

To:

--LAK ACTIVITY ENHANCERS DERIVED FROM EXTRACT OF LENTINUS EDODES MYCELIUM AND LAK ACTIVITY-ENHANCING FORMULATIONS CONTAINING THE EXTRACT--

This certificate supersedes the Certificate of Correction issued May 6, 2008.

Signed and Sealed this

Third Day of June, 2008

JON W. DUDAS
*Director of the United States Patent and Trademark Office*